United States Patent [19]
Weinberger

[11] Patent Number: 6,027,875
[45] Date of Patent: Feb. 22, 2000

[54] RECEPTOR INFECTION ASSAY

[75] Inventor: Cary Alan Weinberger, San Diego, Calif.

[73] Assignee: The Salk Institute for Biological Studies, La Jolla, Calif.

[21] Appl. No.: 07/812,880

[22] Filed: Dec. 20, 1991

Related U.S. Application Data

[63] Continuation of application No. 07/426,894, Oct. 25, 1989, abandoned.

[51] Int. Cl.$^7$ .............................. C12Q 1/68; C12N 5/10
[52] U.S. Cl. ............................... 435/6; 435/325; 435/369
[58] Field of Search ........................... 435/6, 325, 369; 536/27, 23.5; 935/77, 78

[56] References Cited

U.S. PATENT DOCUMENTS 4,981,784  1/1991  Evans et al. ................. 435/6

OTHER PUBLICATIONS

Shackleford, Proc. Natl. Acad. Sci. v. 85, Dec. 1988, pp. 9655–9659.
Shuyer, Biochemistry, W H. Freeman & Co, San Francisco, 1975, p. 761.
Logan et al, Proc. Natl. Acad. Sci, v. 81, Jun. 1984, pp. 3655–3659.
Jones et al, Cell, v. 17, Jul. 1979, pp. 683–689.
Piccini et al, Methods in Enzymology, v. 153, 1987, pp. 545–563.

*Primary Examiner*—Robert A. Schwartzman
*Attorney, Agent, or Firm*—Gray Cary Ware & Freidenrich LLP; Stephen E. Reiter

[57] ABSTRACT

The present invention relates to improvements in a bioassay useful for identifying materials that function as ligands for a hormone or hormone-like receptor protein measured by means of induction of reporter DNA driven by a promoter of a hormone response element. The improvement comprises producing a cell operatively harboring DNA encoding reporter gene and receptor gene by coinfection of a mammalian cell with a viral expression vector. The expedient of this invention permits commercial realization and exploitation of the bioassay system.

20 Claims, 2 Drawing Sheets

RECEPTOR INFECTION ASSAY

RELATED APPLICATION

This application is a continuation of application Ser. No. 07/426,894, filed Oct. 25, 1989 abandoned.

Express reference is made to U.S. patent application Ser. No. 922,585, filed Oct. 24, 1986, abandoned, and to its continuing application U.S. Ser. No. 108,471, filed Oct. 20, 1987, U.S. Pat. No. 5,071,773, counterparts of which exist as published documents by certain jurisdictions outside of the United States, and to U.S. Ser. No. 128,331, filed Dec. 2, 1987 abandoned, and to its continuing application U.S. Ser. No. 276,536, filed Nov. 30, 1988, U.S. Pat. No. 4,981, 784. All of these applications refer in various respects to hormone or hormone-like receptors and compositions thereof, and to methods for their preparation, and use, particularly in novel assay systems. The entire disclosures of each of these applications is hereby incorporated by express reference herein.

FIELD OF THE INVENTION

The present invention relates to novel and improved bioassay systems for identifying and measuring certain materials whose ability to functionally bind to functional receptor proteins is sought to be determined. The novel bioassays hereof incorporate the expedient of using a coinfection method of endowing host cells with DNA functionality so as to produce cell products that are readily available for purposes of the intended bioassay procedure hereof.

BACKGROUND OF THE INVENTION

The patent applications cited supra. disclose, inter alia, the characterization and preparation of various hormone and hormone-like receptors, including steroid, thyroid, and retinoid receptors such as those represented by the glucocorticoid, mineralocorticoid, thyroid, estrogen related and retinoid classes, and specifically, the glucocorticoid, estrogen, aldosterone, and retinoic acid receptors themselves. These specific receptors have been the subject of considerable research and form the particular bases for the inventions disclosed and claimed in those patent applications. Similarly, the extant parallel scientific literature has focused on the specific receptors listed above from among the classes of receptors that are known to exist.

Those applications, although cast in terms generic in sweep, exemplify the use of transfection (transformation) of host cells for operatively introducing the DNA useful for the intended purpose of the bioassay disclosed. Those applications describe the use of bacterial cells, such as *E. coli*, as well as mammalian cells, such as those of the COS line of monkey kidney cells. Those applications do not specifically disclose the use of a lytic or nonlytic system of infection using viral expression vectors.

The use of viral expression vectors has been reported in the art. See Darnell, *Nature* 297, 365 (1982), Thummel et al. *J. Mol. Applied Gen.* 1, 435 (1982) ; Chu et al., *Nature* 289, 378 (1981); Post et al., *Mol. Cell Biol.* 2, 233 (1982); Davidson et al., *J. Virol.* 61, 1226 (1987) and Mackett et al., *PNAS* 79, 7415 (1982). Thus, the literature provides generally the methods and means for producing operative viral expression vectors harboring DNA encoding desired polypeptide, transfecting (infecting) hosts and culturing same so as to produce novel cell lines that produce polypeptides that are heterologous to the endogenous polypeptides of that cell line, and means utilizing such systems for purposes of devising so-called recombinant systems that can be used for the production of heterologous polypeptides, and so forth. Further, Vennstrom et al, *Nature* 340, 242 (1989) used recombinant vaccinia virus to express thyroid hormone receptors and measured via DNA footprinting receptor-DNA binding by use of a restriction fragment containing DNA of the thyroid response element.

In the preparation of recombinant expression systems, an enviable advantage that such virally based systems provide is the generation of copious amounts of the heterologous polypeptide encoded by the viral expression vector. However, documentation will predict that, for example, adenovirus and other viruses retard the synthesis of endogenous proteins required for cell viability. See Beltz, et al, *JMB* 131, 353 (1979). Mechanistically, it is believed that while the virus may not interfere with the normal transcription process, it is believed that the resultant transcripts somehow have difficulty in being transported properly to the cytoplasm where they are translated into polypeptide. Secondly, the viral messenger RNA transcripts are preferentially translated (not solely because of stoichiometry), robbing the cell of energy needed to produce its own endogenous proteins.

The present invention was predicated on the possibility of harnessing the advantages of a viral expression vector based system for use in the bioassay procedures disclosed and claimed in the aforecited patent applications. It was assumed that such viral based expression systems would generate sufficient receptor, and consequently, marker molecules so as to extend laboratory success into commercial reality. However, the disadvantages of viral based expression systems enumerated above evoked the predictably unanswerable question of whether viral DNA would so disrupt the cells in which the bioassay was being utilized that the assay would not work, or not sufficiently, for commercial exploitation. Thus, until the present invention, it remained unpredictable in fact whether the use of viral based expression systems for bioassay procedures that measure the effect of materials for activity as receptor ligands, would result in bioassay systems having commercial viability.

It is thus an object of the present invention to base such ligand binding bioassays using recombinant host cells coinfected with viral based expression vectors harboring DNA operative for bioassay functionality.

SUMMARY OF THE INVENTION

The present invention is directed to improvements in a bioassay system for identifying and measuring putative ligand activity toward hormone or hormone-like receptor polypeptides. The improvements hereof are related to the coinfection of host cells with viral based expression vector (s) harboring DNA encoding the desired functional hormone or hormone-like receptor polypeptide, if necessary where the cell line employed lacks endogenous quantities of said receptor, and DNA encoding a reporter molecule operatively linked to the appropriate, corresponding hormone response element DNA. When host cells are so infected, in accord with the present invention, they remain viable and produce such measurable amounts of reporter molecule, upon induction of the hormone response element by successful receptor putative ligand complex formation when a successful putative ligand material is tested. Successful candidate receptor ligand materials produce reporter without the art-predicted viral induced impairment of the infected host cell. Thus, the information provided by this invention enables the production of harnessed, recombinant bioassay systems useful for their intended purpose of identifying materials having a putative potential as a functional ligand for functional receptor proteins.

The present invention is directed to a method for inducing the expression of DNA encoding a reporter polypeptide, or other desired heterologous polypeptide, comprising inducing transcription of the DNA encoding said polypeptide by the binding to a hormone or hormone-like response element driving such transcription of a complex formed by a corresponding hormone or hormone-like receptor and a corresponding ligand capable of functionally binding to said receptor, in an in vitro setting wherein DNA encoding said receptor and said DNA encoding said reporter or polypeptide are recombinantly expressed in a host cell that has been infected with such DNA via viral based expression vector(s).

The present invention is directed to this novel bioassay improvement using a coinfection of viral based expression vectors, in all aspects, and borrows from relevant recombinant DNA technology for certain basic, known technology for effecting the present invention. These methods comprise also a method of use utilizing such information to devise cells or cell-lines harboring genetic information sufficient for such cells or cell-lines to produce reporter or heterologous polypeptide molecules such that they can be used as such or in an expression system or in bioassays for determining the activity of putative ligands of a desired, chosen hormone or hormone-like receptor against which activity is sought to be determined.

DETAILED DESCRIPTION OF THE INVENTION

B. GENERAL METHODS AND DEFINITIONS

The "hormone or hormone-like receptors" used in this invention include the receptors specifically disclosed, for all species where serial (species to species) cross-hybridization exists, most notably other mammalian receptors, as well as related (e.g., gene family) receptors of the same or cross-hybridizable species that are enabled by virtue of DNA isolation and characterization and use via cross-hybridization techniques from said specific receptors or from identification via immuno cross-reactivity to antibodies raised to determinants of said specific receptors in the usual manner known per se. It also includes functional equivalents of all of the above, including interspecies or intraspecies receptors wherein DNA-binding and/or ligand-binding domains are swapped with one another (so-called chimeric receptors) or otherwise differing in one or more amino acids from the corresponding parent, or in glycosylation and/or phosphorylation patterns, or in bounded conformational structure.

A "hormone response element" is a sequence of DNA that is capable of activation by the DNA-binding domain of an uninhibited, high DNA-binding affinity corresponding hormone or hormone-like receptor, via a complex thereof with an appropriate ligand bound thereto. The hormone response element is generally responsive to a selective hormone, and in the present context that is intended to mean hormone-like materials that similarly so activate the corresponding parent hormone response element. Generally, the hormone response elements are known in the art, or if unknown, their functionality can be determined by knowledge of the sequence, and particularly the DNA binding sequence of the corresponding receptor. By the quoted term is intended hormone response elements known or yet to be discovered that are responsive to the corresponding hormone or hormone-like receptors hereof.

By the term "reporter" is meant polypeptides or their precursor transcripts that can be measured by virtue of their enzymatic, immunological or other properties, such as via spectrophotometric or radio measurement, as examples. Generally, molecules are known in the art and find utility for their intended purpose by virtue of their being measurable by some reproducible physical means known in the art.

"Recombinant host cells" or "host cells" refers to cells that are capable of being operatively infected with the viral based expression vectors of the present invention. Generally, but not necessarily, the most suitable host cells are mammalian host cells and include by way of example only, CHO, Hela, CV1, 293 and KB cells, and because the bioassay system of the present invention is practiced outside of the human biological system, such lines as the COS monkey kidney cell-lines are also useful herein. The test of utility and hence usefulness of any of the myriad of available host cells is whether they can be successfully infected operatively with a particular viral vector in accord with the teachings of the present invention. The cell lines chosen may contain endogenous quantities of a given receptor against which candidate ligands are desired to be tested or they may lack the ability to produce such receptors. In the former case the expression vector will also operatively harbor DNA encoding the receptor, while in the latter case, this is not necessary.

"Expression vector" includes vectors that are capable of expressing DNA sequences contained therein, where such sequences are operatively linked to other sequences capable of effecting their expression. It is implied, although not always explicitly stated, that these expression vectors may be replicable in the host organisms either as episomes or as an integral part of the chromosomal DNA. "Operative", or grammatical equivalents, means that the respective DNA sequences are operational, that is, work for their intended purposes. In sum, "expression vector" is given a functional definition, and any DNA sequence that is capable of effecting expression of a specified DNA sequence disposed therein is included in this term as it is applied to the specified sequence. The invention is intended to include other forms of expression vectors that serve equivalent functions and which become known in the art subsequently hereto. The only limitation in the definition, is that they be viral based such that they are capable of infecting host cells via encapsidation in an operative manner.

"Extrinsic support medium" or "medium" includes those known or devised media that can support the cells in a growth phase or maintain them in a viable state such that they perform the recombinantly harnessed function. See for example, *ATCC Media Handbook*. Ed. Cote et al, American Type Culture Collection, Manassas, Va. (1984). A growth supporting medium for mammalian cells, for example, preferably contains a serum supplement such as fetal calf serum or other supplementing component commonly used to facilitate cell growth and division such as hydrolysates of animal meat or milk, tissue or organ extracts, macerated clots or their extracts, and so forth. Other suitable medium components include, for example, transferrin, insulin and various metals.

In addition to the above discussion and the various references to existing literature teachings, reference is explicitly made to standard textbooks of molecular biology that contain definitions and methods and means for carrying out basic techniques encompassed by the present invention. See, for example, Maniatis, et al., *Molecular Cloning: A Laboratory Manual*, Cold Spring Harbor Laboratory, New York (1982), and the various references cited therein, and in particular, Colowick et al., *Methods in Enzymology*. Volume 152, Academic Press, Inc. (1987). All of the herein cited publications are by this reference hereby expressly incorporated herein.

The foregoing description and following experimental detail set forth the methodology employed initially in producing a bioassay system suitable for identifying and measuring putative ligand binding activity of materials to specific hormone or hormone-like receptors, using the improvement of a recombinant system produced by infecting host cells with viral based expression vectors harboring the appropriate and corresponding DNA encoding the receptor and a reporter molecule, the latter being operatively linked to an appropriate hormone response element. The art-skilled will recognize that by supplying the present information, including the specifics of a viral based coinfection bioassay hereof, it is not necessary, or perhaps even scientifically appropriate, to repeat these details in endeavors to reproduce this work. Instead, they may choose to employ alternative, reliable and known methods, for example, they may synthesize the underlying DNA sequences encoding a particular polypeptide hereof and deploy them within similar or other suitable, operative viral based expression vectors and culture systems. Thus, in addition to supplying details actually employed, the present disclosure serves to enable reproduction of the specific embodiments hereof and others, using means within the skill of the art having benefit of the present essential disclosure. All of such means are included within the enablement and scope of the present invention.

C. DETAILED DESCRIPTION OF PARTICULARLY PREFERRED EMBODIMENTS

The description of the coinfection assay of the present invention demonstrates a rapid, efficient means for examining an unknown compound's ability to activate a nuclear receptor using a bipartite system of adenovirus vectors harboring receptor and reporter genes. The major advantages of using a virus to introduce genes into cells include their capacity to infect virtually one hundred percent of the cells, to obviate the need for a controlled plasmid measuring the efficiency of transfection commonly done during standard assays, and to make the system more amenable to automation by reducing the scale of operation fundamental to testing large numbers of compounds in a bioassay laboratory setting.

The feasibility of the fundamental concept has been demonstrated practicably with viruses harboring the human glucocorticoid receptor (GR) gene and MTV/luciferase reporter genes. The results from this system are extendable to other hormone receptor gene activation systems. Similarly, one can also use other viral vectors such as vaccinia, herpes virus, or any other virus that replicates its genes to high copy numbers in eukaryotic cells.

Graham and Van der Eb's calcium phosphate DNA coprecipitation technique (*Virology* 52, 456 (1973)) was used to introduce essentially wild-type adenovirus DNA and a plasmid containing the left-hand portion of adenovirus into cells. Adenovirus genome is made up of a double-stranded DNA molecule having 35500 base pairs. This is divided into so-called map units, each having 355 base pairs. A map unit is equal to 1 percent of the viral genome. The major late promoter is found at about 16 map units.

The adenovirus DNA had deleted nearly all of the early region of E1A up to the Xba I site at nucleotide 1336 from the left-hand side of the viral DNA. The resultant recombinant virus was produced by taking advantage of the ability of the DNAs to recombine efficiently within infected cells. The starting materials included 293 cells (known to harbor and express complementarily the left-hand end of the adenovirus) (See Graham et al., *J. Gen. Virol.* 36, 59 (1977)), wild-type adenovirus serotype 5, a ColE1 replicon plasmid containing the left-hand end of adenovirus type 5 to fifteen percent at or near the Xho I site, and a plasmid operatively containing the firefly luciferase gene.

The vectors that contain the left-hand end (approximately fifteen percent) of adenovirus type 5 (Logan, et al., *PNAS* 81, 3655 (1984)) were used to generate derivatives that possess the major late promoter sequence of adenovirus to drive expression of heterologous DNA sequence downstream. Those researchers had incorporated the tripartite leader sequence to increase the translational efficiency of the heterologous transcripts.

The foregoing plasmids served as a starting sequence for the coinfection assay hereof. The human glucocorticoid receptor cDNA is driven by the Rous sarcoma virus long terminal repeat promoter with transcription terminated by the SV40 polyadenylation sequence. Firefly luciferase cDNA functioned as the reporter gene sequence with transcription also terminated by the SV40 poly(A) sequence.

The receptor transcription unit was inserted between the Xho I and Bgl II sites of MpCV2 (Logan, et al., supra) in an orientation opposite to that of the adenovirus major late promoter (MLP) (in the early region 1). MpCV2 is the name given herein of the viral vector prepared by and obtained from Logan et al., Supra.

The Xho I and Bgl II sites of MpCV2 were repaired using the Klenow fragment of DNA polymerase and ligated to a double-stranded oligonucleotide encoding a Bam HI site, introducing a Bam HI site such that any desired transcription unit could be easily inserted at that site, producing MpCV3. The reporter transcription unit was inserted at the Bam HI site (that was blunt-ended using Klenow polymerase) of MpCV3.

It was found that without the RSV LTR sequence aberrantly-sized GR protein products were synthesized, probably due to the proclivity of adenovirus to splice RNAs. only when transcription units were inserted in the orientation opposite to the MLP did the synthesis of normal proteins occur. In addition, the presence of the MLP in an antisense orientation potentially inhibits expression of the inserted transcriptional unit. Preferably, therefore, this sequence element should be removed from the plasmid.

The resultant plasmid was partially digested with Cla I because the GR cDNA fragment has a Cla I site and because the sequence joining the plasmid to the viral DNA left hand end has a Cla I site. The longest linear fragment was mixed with the about three to one hundred percent DNA fragment from dl 309 (Jones, et al. *Cell* 17, 683(1979)) and transfected into 293 cells. Graham et al., *J. Gen. Virol.* 36, 59 (1977) (Other adenovirus variants can also be employed; dl 309 was chosen because it was known to express wild-type-like infectious titers.) DNA recombination occurred within the cells to regenerate intact virus. Either mixed lysates can be harvested, or better, plaques can be purified. The mixtures are then tested in a luciferase assay system. (de Wet, et al.,

*Mol. Cell Biol.* 7, 725 (1987)) When infections are done in cells other than 293 cells, that contain complements of the adenovirus DNA, dl 309, or other virus that express the genes deleted in the recombinant virus, must be added in order to complement the deleted recombinant virus functions supplied by the 293 cells.

With the unpurified virus stocks, their ability to measure hormone-responsiveness was accomplished using various adrenocorticosteroid, in the luciferase based assay. Assuming that the titer of the viral stocks was approximately $10^8$ PFU/ML, either 293 cells or CV-1 cells that have low endogenous GR levels were infected with both stocks at a multiplicity of infection equal to ten PFU/cell. At twenty-two hours after infection (empirically determined to be the time when maximal GR synthesis occurs by Western blot measurement of protein), cell lysates were prepared and tested for luciferase activity.

Within the concentration range of $10^{-10}$ and $10^{-5}$ M of corticosteroids, dose response curves were generated that appeared by all qualitative criteria to resemble the binding activities of those glucocorticoids for the receptor protein. Estrogen, thyroid hormone, and retinoic acid were ineffective inducers in this system.

Up to one million RLU relative light units (RLU) were measured per well in a 96-well dish. Because the MLUC3 virus used in these tests was contaminated with wild-type virus, perhaps by as much as ninety-nine percent, the response level achieved should be considerably higher.

D. EXAMPLES

1. Reference Example

Adenovirus consists of a double-stranded DNA molecule packaged within an icosahedral capsid that consists predominantly of two protein monomeric capsomers called hexon and penton base. Extending from the junctions of these faces are fibers having adhesion protein globules at the end distal from the vertices. It is believed that these fiber proteins are responsible for virus adsorption to cells of certain types. Following virus adsorption, the viral particle may enter the cell by pinocytosis and travel along microtubules wherein the viral DNA is uncoated by a series of steps within the cell during the virus particle's migration to the cell nucleus wherein the viral DNA is replicated to high copy numbers. Viral DNA replication occurs at 12–15 hours after virus adsorption to typical host cells commonly used in the laboratory such as those designated HeLa. As noted above, the rapid replication of viral DNA within the infected cell interferes with normal cell function, probably by competing with cellular DNA replication and inhibiting the transport of host messenger RNAs to the cytoplasm. Eventually the infected cell detaches from the plate substrate and exhibits cytopathic effects which is at least partially due to the action of penton base, releasing newly replicated viral DNA copies packaged within newly synthesized capsids that may infect adjacent cells. This phenomenon of generating new rounds of viral particles is the essence of viral infection and often accounts for the attendant pathological states.

Adenovirus DNA is made up of about thirty-five thousand base pairs with a covalently-linked 55 kDa viral polypeptide bound at each of its two 5' ends. Along the DNA sequence have been mapped transcription units that become selectively activated at particular times during the virus infection. These have been designated E1A, E1B, E2, E2, E3, and E4 for those producing mRNAs synthesized at early times after infection (before viral DNA replication). Each of the early transcription units encodes a polypeptide responsible for initiating cascades of biochemical events culminating in the production of many copies of viral DNA. For instance, the E1A region is believed to produce or encode protein products that facilitate transcription of the viral genes designated E1B, E2, E3, and E4. Differential splicing of transcripts from the E2 gene eventually serves to generate two protein products, a 72 kDa single-stranded DNA binding protein and a viral DNA polymerase required for viral DNA replication. The E3 region encodes a glycoprotein with unknown function, but it is not essential to support virus growth in cell culture because wild-type levels of virus are achieved when this gene is mutated or deleted from the viral DNA. The E4 region encodes a protein whose precise function is unknown but is required for normal virus functions.

Following viral DNA replication a long precursor RNA transcript is synthesized from the major late promoter which initiates rightward-reading transcription from 16 map units on the standard adenovirus map. Five sets of 3'-coterminal mRNAs are processed from this precursor transcript, each mRNA derived from a single precursor RNA. These have been designated L1, L2, L3, L4, and L5 for RNAs transcribed at late times (after viral DNA replication). For the most part, they encode polypeptides which are assembled into the virion capsid. For example, L2 encodes penton base, L3 codes for hexon protein while L5 is responsible for the synthesis of fiber protein. Each of the mRNAs has a tripartite leader sequence spliced on their 5' ends that increases the translational efficiency of these viral late mRNAs.

The host cells commonly infected by both adenovirus serotypes 2 and 5, routinely used by various investigators for studies of eukaryotic gene expression, include cells derived from a human cervical carcinoma known as HeLa cells as well as cells derived from African green monkey kidney called CV-1 cells. The yields of virus are substantially lower from CV-1 cells when compared with infected HeLa cells. This is due to a defect in fiber mRNA processing. The reduced virus yield can be overcome by coinfection with another DNA tumor virus called SV40. CV-1 cells, despite their inability to support virus infection, can be used for coinfection studies because they permit normal virus replication, and for the example cited here, they have low endogenous glucocorticoid receptor levels.

It can be seen that in the construction of vectors useful in the bioassay system disclosed in the present invention, focusing on the adenovirus genome, it is important that the E1A, E2, and E4 regions remain untampered with. The E3 region, not being essential for viral replication in cell culture systems, is an ideal location to insert DNA of choice for the given bioassay system devised.

In the present work, the foreign DNA was inserted usually in the E1 or E2 sites therefore destroying normal viral function. Because of that phenomenon the present work employed host cells that complement growth defective viral DNA, for example, 293 cells (human embryonic kidney cells) that fortuitously contain zero to thirty percent (map units) of adenovirus. Therefore, when employing 293 cells one can insert the foreign DNA necessary for the present bioassay system at the E1A, E1B and E3 regions because the 293 cells fortuitously complement E1A and E1B function and E3 is not essential for viral replication and functionality. This region occurs in the area of zero to fifteen map units of the plasmid and is thus the designated work-horse region for foreign DNA insertion when employing 293 cells.

Thus, the major late promoter without the tripartite region could be used as a promoter for the foreign gene expression of the receptor of choice. Similarly, the RSV without the tripartite could be used as the promoter of the receptor or the receptor promoter itself could be employed although this is thought to be less efficient.

2. Model Example

The starting plasmid MpCV2 was constructed in the following manner. Adenovirus DNA was digested with S1 nuclease and repaired with the Klenow fragment of *E. coli* DNA polymerase I. Following Xho I digestion, the Xho I-C fragment was isolated and inserted between the Klenow-repaired Hind III and the Sal I sites of pBR322 to construct pXho I-C plasmid. To construct MpCV2, a three fragment ligation was assembled using the following DNA fragments: the large fragment of pxho I-C from Eco RI to Xho I; a 354 base pair fragment spanning the Eco RI (at the extreme left hand end of adenovirus to Sac II site (354 in the E1A region of the adenovirus map); and a third DNA fragment from Sac II to Xho I derived from the left hand end plasmid used to construct sub 360-L,2,3 virus containing the major late transcriptional control region and the tripartite leader sequences (Logan et al., *Proc. Nat. Acad. Sci. USA* 81, 3655 (1984)), MpCV3 was generated by digesting MpCV2 DNA with Xho I and Bgl II and repairing with Klenow fragment of DNA polymerase. A Bam HI linker fragment was ligated to these ends, the mixture was digested with Bam HI, and the large linear DNA fragment was isolated, ligated and used to transform bacteria to produce MpCV3.

To generate recombinant adenovirus hGR4, the following construction scheme was used. The precursor to plasmid alpha pRShGR, which had not had its single Bam HI site destroyed at the 3' end of the SV40 polyadenylation signal was used (Giguere et al, *Cell* 46, 645 (1986)). This plasmid was digested with Nde I, repaired with the Klenow fragment of DNA polymerase I, and a palindromic DNA linker fragment containing a Bam HI site was ligated to this DNA. Following Bam HI digestion, the 2.6 kilobase pair DNA fragment containing the RSV LTR/hGR/SV40 poly (A) addition signal transcription unit was isolated and ligated to Bam HI-digested, bacterial alkaline phosphatase-treated MpCV3 DNA fragment. A clone with the glucocorticoid receptor transcription unit oriented opposite with respect to the major late promoter in MpCV3 called MpCV3-hGR4 was isolated and used to construct recombinant virus.

Recombinant glucocorticoid receptor virus hGR4 was constructed by the overlap method of recombination as described by Chinnadurai et al., *J. Virol.* 32, 623 (1979). A deletion mutant of adenovirus type 5 called dl 309 was used as the starting material for preparation of virus DNA (Jones et al., *Cell* 13, 181 (1978)). dl 309 DNA was digested with Cla I and Xba I to completion and the large fragment from 1336 to the right hand end was isolated by sucrose gradient centrifugation (Stow, *J. Virol.* 37, 171 (1981)) This was mixed with MpCV3-hGR4 plasmid DNA digested partially with Cla I to linearize most of the plasmid DNA and used to transfect 293 cells that contain and express the left hand 11% of adenovirus type 2. (Note that since two Cla I sites are found in MpCV3-hGR4, one at the junction between the plasmid and the virus extreme left hand end sequences, partial digestion with Cla I had to be carried out to generate a subpopulation of molecules with the glucocorticoid receptor Cla I site intact). Virus harvested from these transfected cells was expanded and the stocks were assayed for receptor function in conjunction with the reporter recombinant virus stocks generated as described below.

To generate recombinant reporter virus MLUC3, a similar strategy was used. The starting plasmid was generated using MTV-LUC described in Hollenberg et al., *Cell* 55, 899 (1988). The 4.2 kilobase pair Pvu II DNA fragment (containing the mouse mammary tumor virus LTR linked to firefly luciferase downstream of which is located the SV40 polyadenylation sequence) was isolated from MTV-LUC and ligated to Bam HI, Klenow-repaired, bacterial alkaline phosphatase-treated MpCV3 DNA. A clone pAd3/MLUC with the luciferase transcription unit oriented opposite to the major late promoter was isolated and used to construct MLUC3 virus.

MLUC3 virus was constructed in the same fashion as hGR4 virus by partially digesting plasmid pAd3/MLUC DNA with Cla I because in addition to the Cla I site at the left hand end of adenovirus, it also contains a Cla I site in the coding region of the luciferase gene. As described above, this DNA was mixed with the large Xba I fragment from dl 309 and used to transfect 293 cells. Virus lysing these cells was expanded by reinfecting new plates of cells to generate high titer stocks.

The coinfection assay was carried out in the following manner. Twelve well dishes were seeded with 293 cells at a density of $1.2 \times 10^5$ cells per well and grown in Dulbecco's modified Eagle's medium (DME) supplemented with 10% fetal calf serum. Assuming that the hGR4, MLUC3, and dl 309 virus stocks were $10^8$ PFU/ml, the next day cells were infected with various combinations of these stocks in triplicate at a multiplicity of infection corresponding to 50. Dexamethasone dissolved in 50% ethanol or the control vehicle alone were each diluted into DME supplemented with 10% charcoal-adsorbed fetal calf serum at a final concentration of 0.1 $\mu$M. These mixtures were added to cells adsorbed with virus for thirty minutes. Cells were harvested at 18, 22 and 89 hours after infection by scraping them from the plate and washing the cell pellets in phosphate-buffered saline, and resuspending them in 100 microliters of 100 mM $K_2HPO_4$ (pH 7.8), 1 mM dithiothreitol). Cell lysates were prepared by three cycles of sequential freezing and thawing in a dry ice/ethanol and 37° C. baths. Cell debris was pelleted by centrifugation in a microcentrifuge for 5 minutes at 4° C. Ten microliters of these cell lysates were dissolved in 350 microliters of 100 mM $K_2HPO_4$ (pH 7.8) containing 5mM ATP and 15 mM $MgCl_2$. Luciferase enzyme activity was assayed by automatic injection of 1 mM d-luciferin (Analytical Luminescence Laboratories) as described in de Wet et al. *Mol. Cell. Biol.* 7, 725 (1987) using a Berthold luminometer.

The orientation is reversed relative to the major late promoter with the RSV long term repeat promoter driving the expression of the human glucocorticoid receptor DNA terminating with SV40 polyadenylation sequence. This orientation removes the tripartite leader from functioning in its usual manner. A separate vector for the receptor DNA is constructed similarly. The two vectors are separately used to infect 293 cells. First, 293 cells are infected with the vector bearing the human glucocorticoid receptor DNA. Successful infection can be tested by picking plaques and doing a Western analysis with human glucocorticoid receptor antibodies or one can measure the ligand binding properties of the extracts or one can do a restriction map analysis to assure proper infection with the human glucocoid receptor adenovirus DNA. Successfully infected cells are then infected with the reporter virus vector. Alternatively, both vectors could be mixed on, for example, 293 cells. Where host cells not bearing a complement of the adenovirus genome are used, one may coinfect with wild-type virus in order to supply the missing complement. After coinfection, maximum expression of the receptor thus creating optimal time for the bioassay test, occurs at about twenty-two hours. The material to be tested may either be added in at the beginning or at such twenty-two hour period. The cells are then tested for measurement of the reporter activity. In the case of the exemplified luciferase gene, that measurement takes the form of quantitating light emission from luciferin oxidized by any luciferase present.

Example 1: GR Expression with Recombinant Adenovirus

To begin constructing the adenovirus recombinants expressing receptor genes, a plasmid called MpCV3 was used that contains the left-hand 15% of Ad5. It is a mosaic including the major late promoter (MLP) downstream from which is positioned the tripartite leader sequence. Foreign DNA sequences can be inserted at the unique Bam HI site. A human glucocorticoid receptor cDNA was inserted behind the MLP with an SV40 polyadenylation signal defining a transcription termination site. (Giguere, et al., Cell 46, 645 (1986)) The glucocorticoid receptor transcription unit was inserted at the Bam HI site of MpCV3 in two orientations. This plasmid DNA was linearized adjacent to the viral inverted terminal repeat using Cla I partial digestion and cotransfected on 293 cells with a 3-100% viral DNA fragment from dl 309. (Stow, J. Virol. 37, 171 (1981) This deletion mutant contains a single Xba I site at 3.8 map units and a Cla I site at 2.9 map units. Digesting the viral DNA with a combination of Cla I and Xba I reduces the contaminating wild-type virus dl 309 background. When both DNAs are taken up by competent cells, strand exchange between the viral and plasmid DNAs results in the formation of recombinant adenovirus.

Figure 1A:
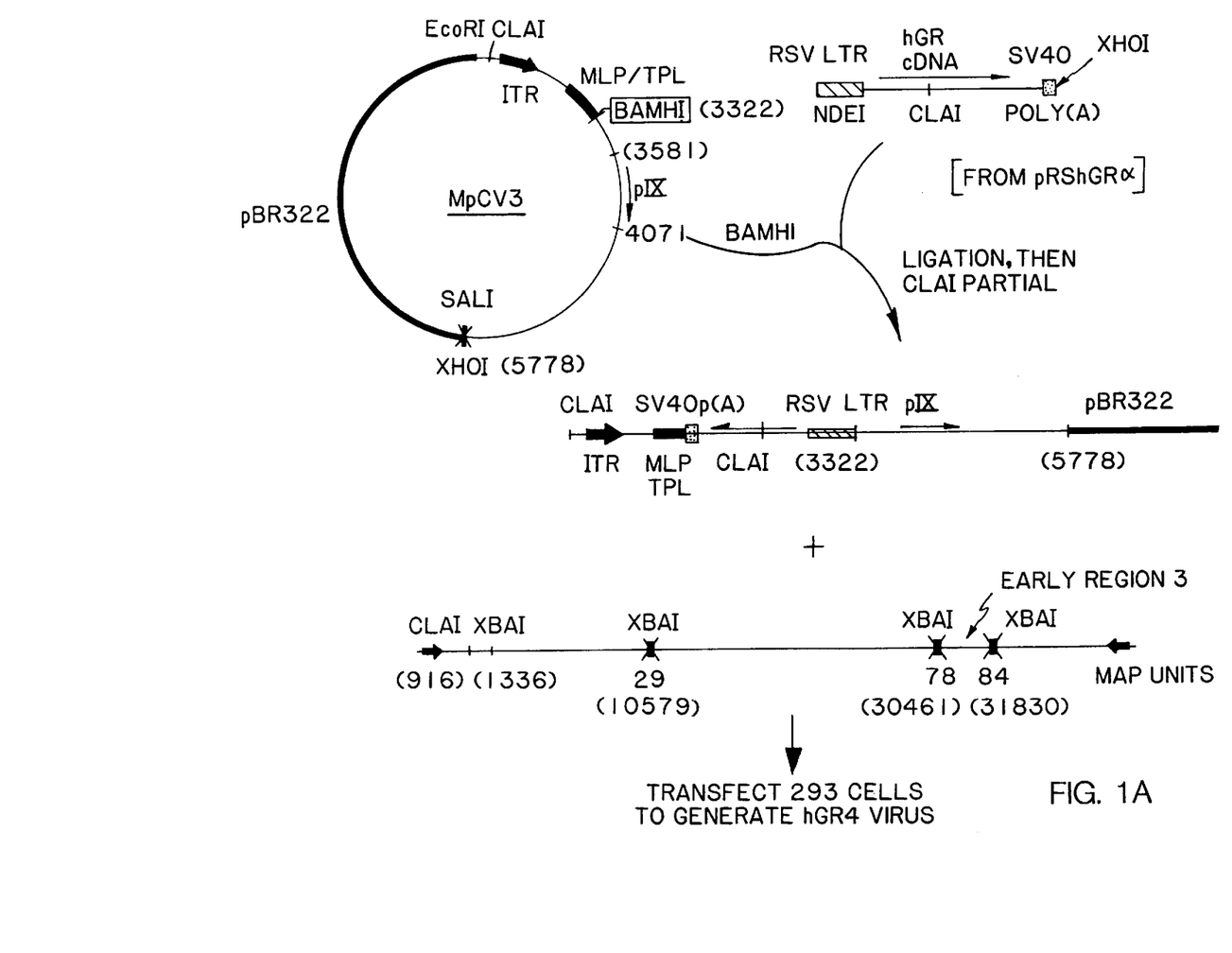
FIGS. 1A–1B depict the strategy of expression vector construction (A) and the results of GR expression in infected 293 cells (ATCC NO. CRL-1573, available from ATCC, 10801 University Boulevard, Manassas, Va., 20110 (B).
Figure 1B:
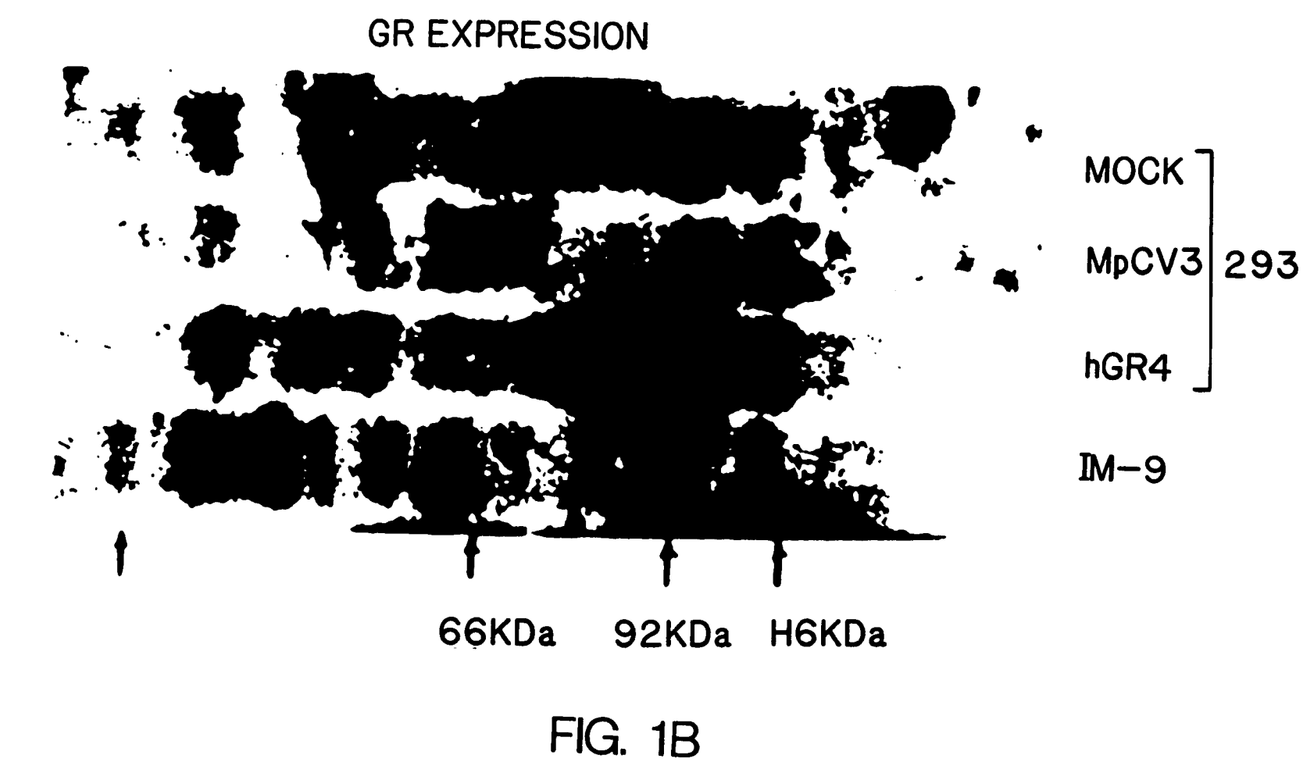

The recombinant virus hGR4 (otherwise variously referred to as hGRAd) obtained was tested for its ability to express hGR. Cell lysates were prepared at late times post infection (about 18 pours p.i.), and analyzed by immunoblotting with a polyclonal peptide-directed antiserum specific for the hGR. A truncated polypeptide product (~70 kDa relative to 94 kDa for wild-type GR) was seen. Conceivably, aberrant splicing of transcription products was responsible for producing this smaller GR. Therefore, the GR TU (transcription unit) reading opposite (leftward reading with respect to the orientation of the E1A and E1B genes) was examined in a recombinant called hGR4 (see FIG. 1 for virus construction strategy and receptor expression). Lysates prepared from hGR4-infected cells at 18 hours p.i. revealed a 94 kDa polypeptide product comigrating with GR found in IM-9 cells. (Harmon, et al., Cancer Research 44, 4540 (1984)) By quantitating nitrocellulose strips corresponding to these bands, a 50-fold increase in receptor number is detected in hGR4-infected 293s when compared with IM-9 cells. Since IM-9s express about 100,000 GR molecules per cell, approximately 5 million receptors are synthesized in hGR4-infected cells.

Example 2: Functional Assay Using Recombinant Receptor and Reporter Viruses

A reporter virus (MLUC3; also variously referred to as Ad3MLUC, MpCV3MTV-LUC-Ad and ADMLUC) was constructed containing the mouse mammary tumor virus LTR linked to the firefly luciferase cDNA with an SV40 polyadenylation signal (Hollenberg, et al., Cell 55, 899 (1988)) similar to the receptor virus hGR4 above. The two viruses, hGR4 and MLUC3, were coinfected into 293 cells growing in DMEM suplemented with 10% charcoal adsorbed fetal calf serum $\pm 10^{-7}$ M dexamethasone (dex), and cellular extracts were prepared by Triton X-100™ brand non-ionic surfactant lysis at 22 hours after infection. (Williams, et al., Anal. Biochem 176, 28 (1989)) These were tested for luciferase activity by incubating with ATP and luciferin in a suitable buffer system. (de Wet, et al., Mol. Cell Biol. 7, 725 (1987)). Light liberated in this reaction was measured using a luminometer. Using MLUC3, a 10-fold stimulation of luciferase activity was detected only in the presence of $10^{-7}$ M dex. Furthermore, this response was enhanced an additional 5-fold by coinfection with hGR4 and not with parental virus dl 309. The response was mimicked by other natural and synthetic adrenocorticosteriods, namely, cortisol, corticosterone, aldosterone, and estrogen. The biological activity seen with these compounds is similar in kind to that obtained by the cotransfection method and parallel the rank hormone binding activities of each of these compounds for the GR. See Table I.

Since viral DNA recombination in adenovirus-infected cells occurs frequently, one question concerns the stability of the foreign gene in the receptor virus stock. After the virus stock was passaged twice, six representative receptor virus plaques were isolated from the hGR4 stock and tested in the coinfection assay with luciferase gene-containing virus MLUC3. All six of the hGR4 plaque isolates produced measured transcriptional responses as great as the original virus stock.

TABLE I

ADENOVIRUS CO-INFECTION RESULTS
PART I: RESPONSE AND COEFFICIENT OF VARIATION (CV) OF
CELL LYSATE; 20 UL/200 UL OF LYSATE WAS ASSAYED

| HRS AFTER CO-INFECTION | LIGAND | CO-INFECTION: ADENOVIRUS/GENES | | | |
|---|---|---|---|---|---|
| | | HGR DL309 | MTV-LUC DL309 | HGR MTV-LUC | DL309 |
| 18 HRS | DEX $10^{-7}$M | 33 (29%) | 19130 (13%) | 72864 (37%) | 32 (5%) |
| (293 CELL LYSATE) | DEX 3 × $10^{-9}$ | 35 (28%) | 3643 (20%) | 30015 (29%) | 28 (5%) |
| | SOLVENT | 31 (31%) | 2311 (16%) | 1698 (20%) | 29 (5%) |
| 22 HRS | DEX $10^{-7}$M | 42 (38%) | 24215 (4%) | 90718 (18%) | 43 (11%) |
| (293 CELL LYSATE) | DEX 3 × $10^{-9}$ | 40 (19%) | 5095 (12%) | 48858 (14%) | 42 (22%) |
| | SOLVENT | 42 (8%) | 3608 (9%) | 2172 (6%) | 44 (15%) |
| 89 HR | DEX $10^{-7}$M | 27 (4%) | 151 (23%) | 1065 (7%) | 23 (7%) |
| (293 CELL LYSATE) | DEX 3 × $10^{-9}$ | 22 (14%) | 53 (48%) | 1246 (68%) | 22 (24%) |
| | SOLVENT | 22 (19%) | 47 (50%) | 61 (48%) | 24 (16%) |

Example 3: Cellular Host Range Displaying Transcriptional Response in Coinfection Assay Similar biological responses were noted when similar coinfection protocols were used for other cell-lines, including CV-1 and HeLa. A good response is achieved, provided that wild-type adenovirus supplies helper E1A and E1B functions deleted from the recombinant viruses. A wide range of human and rodent cell lines thus serve as suitable hosts for these viral vectors, an important factor in searching for cell-lines with low expression levels of a particular receptor.

One of the most useful aspects of this method is its extreme sensitivity. As a result, very small amounts of cellular material can be assayed. Activities of one million relative light units (RLU), with backgrounds of 10,000 RLU, have been obtained from a single well of a 96-well microliter dish containing approximately 30,000 cells. The low coefficient of variation (<10) between sample points is an additional attractive feature of the system. This sample reproducibility provides a significant advantage over the cotransfection method of testing hormone activation. In addition, the use of detergents such as Triton X-100™ brand non-ionic surfactant permits direct lysis of infected cells directly on the plate, which expedites the processing of large amounts of material. The only subsequent manipulation required is liquid transfer to a luminometer measuring instrument.

Example 4: Detection of Glucocorticoids in Microanalytic Quantities

Cells were infected with hGR4 and MLUC3 recombinant adenoviruses in the presence of varying concentrations of cortisol from $10^{-11}$ M to $10^{-5}$ M in 3-fold dilution steps. At 18 hours p.i., lysates were prepared and luciferase activity was measured. Approximately 10% of the maximal transcriptional response was detected at $10^{-8}$ M cortisol. Since standard assay volumes are 200 μl per well in a 96 sample microliter dish, this represents about $2 \times 10^{-12}$ mole or about 0.6 ng of cortisol.

SUMMARY OF THE DISCLOSURE

The foregoing description details specific methods that can be employed to practice the present invention. Having detailed specific methods initially used to identify, characterize, prepare and use the viral based expression vectors in a coinfection bioassay hereof, and a further disclosure as to specific details thereof, the art-skilled will well enough know how to devise alternative reliable methods for arriving at the same information and for extending this information to other equivalent viral based bioassay coinfection systems. Thus, however detailed the foregoing may appear in text, it should not be construed as limiting the overall scope hereof; rather the ambit of the present invention is to be governed only by the lawful construction of the appended claims.

I claim:

1. A bioassay for identifying compounds which function as ligands for functional receptor proteins, said bioassay comprising:
   (1) culturing mammalian cells in a medium containing test compound(s); wherein said cells produce functional receptor protein(s); and wherein said cells have been infected with a recombinant virus comprising DNA encoding an operative hormone response element operatively linked to DNA encoding a reporter, and
   (2) monitoring said cells for expression of the reporter as an indication of the ability of test compound to act as a ligand for said receptor protein.

2. A bioassay according to claim 1 wherein said mammalian cells are coinfected with a first recombinant virus comprising:
   DNA encoding said functional receptor protein and a second recombinant virus comprising
   DNA encoding a hormone response element operatively linked to DNA encoding a reporter; wherein said hormone response element is responsive to the functional receptor protein.

3. A bioassay according to claim 1, wherein the hormone response element is selected from wild-type, engineered or synthetic glucocorticoid response element, thyroid response element, mineralocorticoid response element, estrogen response element, Vitamin D response element or retinoic acid response element.

4. A bioassay according to claim 1, wherein the recombinant virus is derived from viral DNA selected from vaccinia virus, herpes virus or adenovirus.

5. A bioassay according to claim 1 wherein said functional receptor protein is a chimeric receptor protein.

6. A bioassay according to claim 2, wherein said functional receptor protein is human glucocorticoid receptor and the expression of said protein is controlled by a Rous sarcoma virus long terminal repeat promoter with transcription terminated by a SV40 polyadenylation sequence.

7. A bioassay according to claim 3, wherein the recombinant virus comprises mouse mammary tumor virus operably linked to a luciferase gene.

8. A bioassay according to claim 4, wherein the recombinant virus is wild-type adenovirus serotype 5 and the mammalian host cells are 293 cells.

9. A bioassay according to claim 6, wherein the reporter is firefly luciferase, encoded by firefly luciferase DNA, the expression of which is controlled by a mouse mammary tumor virus long terminal repeat sequence with transcription terminated by a SV40 polyadenylation sequence.

10. A bioassay according to claim 8, wherein the functional receptor protein is human glucocorticoid receptor.

11. A bioassay according to claim 9, where DNA encoding said receptor is inserted between the XhoI and BglII sites of the recombinant virus MpCV2 in an orientation opposite to that of the adenovirus major late promoter and DNA encoding said reporter is inserted into the BamHI site of the recombinant virus MpCV3 in an orientation opposite to that of the adenovirus major late promoter.

12. A bioassay according to claim 10, wherein the reporter is luciferase.

13. A bioassay according to claim 11, wherein the mammalian cells are 293 cells.

14. A method for identifying compounds which function as ligands of functional receptor proteins in a cell, said method comprising:
   contacting mammalian cells with at least one test compound; wherein said cells produce functional receptor protein(s); and wherein said cells have been infected with a recombinant virus comprising DNA encoding an operative hormone response element operatively linked to DNA encoding a reporter, protein and
   identifying those compound(s) which function as ligand(s) for said receptor protein by monitoring expression of the reporter protein in the presence and absence of test compound.

15. A method according to claim 14 wherein said functional receptor protein is provided by infecting said mammalian cells with a recombinant virus comprising DNA encoding functional receptor protein.

16. A method according to claim 14, wherein the mammalian cells are 293 cells.

17. A method according to claim 15, wherein said functional receptor protein is a chimeric receptor protein.

18. A method according to claim 16, wherein the DNA encoding the reporter protein is a luciferase gene.

19. A method according to claim 18, wherein the hormone response element is a glucocorticoid response element.

20. A method according to claim 19, wherein the recombinant virus is derived from adenovirus.

* * * * *